United States Patent [19]

Katz

[11] 3,936,528

[45] Feb. 3, 1976

[54] ANALGESIC FORMULATIONS HAVING ENHANCED THERAPEUTIC ACTIVITY

[75] Inventor: Martin Katz, Palo Alto, Calif.

[73] Assignee: Syntex Corporation, Palo Alto, Calif.

[22] Filed: Feb. 13, 1974

[21] Appl. No.: 442,004

[52] U.S. Cl. .............. 424/260; 424/308; 424/311; 424/317
[51] Int. Cl.² .................. A61K 31/19; A61K 31/22; A61K 31/235, A61K 31/485
[58] Field of Search ......... 424/300, 317, 260, 308, 424/311; 260/520

[56] References Cited
UNITED STATES PATENTS

| | | | |
|---|---|---|---|
| 3,683,015 | 8/1972 | Dyson | 260/520 |
| 3,749,797 | 7/1974 | Miller | 424/316 |
| 3,800,041 | 3/1974 | Miller | 424/273 |

OTHER PUBLICATIONS

American Drug Index, 1970, p. 208.

*Primary Examiner*—Stanley J. Friedman
*Attorney, Agent, or Firm*—Joseph I. Hirsch; William B. Walker

[57] ABSTRACT

This application describes analgesic formulations including d 2-(6-methoxy-2-naphthyl)propionic acid, or a pharmaceutically acceptable salt or ester thereof, in combination with at least one central nervous system active analgesic compound. Analgesic activity of the combination is greater than that obtained with either of the components alone, thus demonstrating enhanced analgesia which can be obtained therewith.

16 Claims, No Drawings

ANALGESIC FORMULATIONS HAVING ENHANCED THERAPEUTIC ACTIVITY

FIELD OF THE INVENTION

This invention relates to an analgesic formulation including d 2-(6-methoxy-2-naphthyl)propionic acid, or a pharmaceutically acceptable salt or ester thereof, in combination with at least one central nervous system active analgesic compound.

BACKGROUND OF THE INVENTION

Prior to this invention, it was heretofore known to provide analgesic compositions having improved analgesic properties by combining α-d-propoxyphene with namoxyrate or indomethacin; for example, see United States No. 3,749,797 or Great Britian No. 1,278,040, respectively.

SUMMARY OF THE INVENTION

The present invention relates to analgesic formulations having enhanced analgesic activity and including d 2-(6-methoxy-2-naphthyl)propionic acid, or a pharmaceutically acceptable salt or ester thereof, in combination with at least one central nervous system active analgesic compound. It has been found that the analgesic activity of the combination of d 2-(6-methoxy-2-naphthyl)propionic acid and the central nervous system active analgesic compound, for example, an analgesic as represented by opium and the opium alkaloids, such as, for example, codeine sulfate, codeine phosphate, morphine, morphine sulfate, hydromorphone, oxymorphone, meperidine, α-d-propoxyphene or α-d-propoxyphene napsylate, is greater than can be obtained with either of the components alone, thus demonstrating enhanced analgesia which can be obtained with the combined mixture.

2-(6-Methoxy-2-naphthyl)propionic acid, the pharmaceutically acceptable salts and esters thereof, and methods for their preparation are described in copending application Ser. No. 372,028, filed June 21, 1973, copending application Ser. No. 394,751, filed Sept. 6, 1973, and U.S. Pat. Nos. 3,651,106; 3,652,683; 3,658,858; 3,658,863; and 3,663,584. Resolution of 2-(6-methoxy-2-naphthyl)propionic acid to yield the optical isomers thereof, including d 2-(6-methoxy-2-naphthyl)propionic acid is shown in U.S. Pat. No. 3,683,015 and copending applications Ser. Nos. 279,329, filed Aug. 10, 1972, and 350,193, filed Apr. 11, 1973. To the extent necessary to complete the disclosure of this application, or to make any portion hereof complete and fully understandable, all or any part of the aforementioned patents or pending applications are incorporated herein by reference.

The term "pharmaceutically acceptable salts" refers to those salts of d 2-(6-methoxy-2-naphthyl)propionic acid prepared from pharmaceutically acceptable non-toxic bases including inorganic bases and organic bases. Salts derived from inorganic bases include the sodium, potassium, lithium, ammonium, calcium, magnesium, ferrous, zinc, manganous, aluminum, ferric, and manganic salts, and the like. Salts derived from organic non-toxic bases include salts of primary, secondary, tertiary, and quaternary amines, substituted amines, including naturally-occurring substituted amines, cyclic amines, and basic ion-exchange resins, such as triethylamine, tripropylamine, ethanolamine, 2-dimethylaminoethanol, 2-diethylaminoethanol, lysine, arginine, histidine, caffeine, procaine, N-ethylpiperidine, hydrabamine, choline, betaine, ethylenediamine, glucosamine, methylglucamine, theobromine, piperazine, piperidine, and the like.

The term "pharmaceutically acceptable esters" refers to the alkyl esters of d 2-(6-methoxy-2-naphthyl)-propionic acid wherein the alkyl group has from 1 to 22 carbon atoms and, accordingly, includes the methyl, ethyl, propyl, isopropyl, butyl, t-butyl, pentyl, isopentyl, cyclopentyl, hexyl, cyclohexyl, octyl, nonyl, tridecyl, isotetradecyl, pentadecyl, isohexadecyl, heptadecyl, eicosyl, and docosyl esters, and the like.

Administration of the formulation of the present invention can be via any of the accepted modes for the administration of agents for the treatment of pain. Thus, administration can be, for example, orally, parenterally, intraveneously, or rectally, in the form of solid, semi-solid, or liquid dosage forms, such as, for example, tablets, suppositories, pills, capsules, powders, liquid solutions, suspensions, or the like, preferably in unit dosage forms suitable for simple administration of precise dosages. The formulations of this invention will include a conventional pharmaceutical carrier or excipient, d 2-(6-methoxy-2-naphthyl)propionic acid, or a salt or ester thereof, and the other analgesic compound, and in addition, may include other pharmaceutical agents, adjuvants, etc.

The preferred manner of administration is oral using a convenient daily dosage regimen which can be adjusted according to the degree of affliction. For such oral administration, a pharmaceutically acceptable non-toxic formulation is prepared by admixture of the active components with any of the normally employed pharmaceutical excipients, such as, for example, pharmaceutical grades of mannitol, lactose, starch, calcium sulfate, dicalcium phosphate, magnesium stearate, sodium saccharin, talcum, cellulose, glucose, sucrose, magnesium carbonate, aluminum hydroxide, and the like. Such compositions take the form of tablets, pills, capsules, powders, sustained release formulations, suspensions, solutions, and the like.

The active components may be formulated into a suppository using, for example, polyoxyethylenes, such as, Carbowax 4000, Witepsol H-15 (triglycerides of saturated fatty acids; a product of Riches-Nelson, Inc., New York, N.Y.) cocoa butter, etc., as the suppository base or carrier. Liquid pharmaceutically administrable compositions can, for example, be prepared by dissolving, dispersing, etc., the active components and any optional pharmaceutical adjuvants in a carrier, such as, for example, water, saline, aqueous dextrose, glycerol, propylene glycol, ethanol, and the like, to thereby form a solution or suspension of the active components in the liquid carrier. If desired, the pharmaceutical formulation may also contain minor amounts of non-toxic auxiliary substances such as wetting or emulsifying agents, pH buffering agents, preservatives, and the like, such as, for example, sorbitan monolaurate, triethanolamine oleate, sodium acetate, methyl paraben, etc.

Actual methods of preparing such dosage forms are known, or will be apparent, to those skilled in this art; for example, see Remington's *Pharmaceutical Sciences*, Mack Publishing, Easton, Pa., 14th edition, 1970. The formulation to be administered will, in any event, contain a pharmaceutically acceptable carrier and, in admixture therewith, a quantity of the active components in a pharmaceutically effective amount for relief of pain in accordance with the teachings of this invention.

Generally, the amount of d 2-(6-methoxy-2-naphthyl)propionic acid and the central nervous system active analgesic compound to be used in the practice of this invention will correspond to those amounts which are suitable for use individually; however, since the combination exhibits enhanced analgesia, it is possible to reduce the total amount of the active components administered to levels which are, by themselves, inactive or insufficiently active, yet retaining desired analgesic activity, or maintain the same dosage rate (as used individually) while attaining greater analgesia. With regard to d 2-(6-methoxy-2-naphthyl)propionic acid, a daily dose (per os) from about 0.1 mg. to 20 mg. per kilogram of body weight, generally from about 1 mg. to about 10 mg. per kilogram of body weight, is satisfactory when the aforementioned compound is used alone as an analgesic agent. The amount of the central nervous system active analgesic agent to be used in combination with the d 2-(6-methoxy-2-naphthyl)propionic acid can be determined with reference to the amount thereof which is used when such a compound is administered alone. However, as indicated above, the amount of each active component in the combination can be reduced in view of the enhanced analgesia which can be obtained with the combination. Exemplary formulations are 250–500 mg. of d 2-(6-methoxy-2-naphthyl)propionic acid and 15–65 mg. codeine sulfate or 32–65 mg. α-d-propoxyphene hydrochloride. In place of the d 2-(6-methoxy-2-naphthyl)propionic acid there can be used 250–550 mg. of the sodium salt of d 2-(6-methoxy-2- naphthyl)propionic acid. Such formulations can be, for example, administered (per os) 3 times per day. In any event, the combined formulation will generally include about 50 to about 750 mg. of d 2-(6-methoxy-2-naphthyl)propionic acid.

DESCRIPTION OF SPECIFIC EMBODIMENTS

The following Examples are given to enable those skilled in this art to more clearly understand and practice the present invention. They should not be considered as a limitation upon the scope of the invention but merely as being illustrative and representative thereof.

In the following Examples, the analgesic activity of various formulations including d 2-(6-methoxy-2-naphthyl)propionic acid and either codeine sulfate or propoxyphene is compared with the analgesic activity of the compounds used individually and against a control situation where no medication is administered. The test used is a mouse writhing test, which consists of orally administering the compound or combination formulation to be tested by gavage in an aqueous vehicle at time 0 to 18–20 gram male Swiss-Webster mice. Twenty minutes later 0.25 ml. of a 0.02% solution of phenylquinone prepared by dissolving 4 mg. of phenylquinone in 0.5 ml. absolute ethanol, and adding 19.5 ml. warmed distilled water to the ethanol solution is injected intraperitoneally. This solution induces writhing. The animals are then observed for the next 10 minutes for writhing.

End point: the total number of mice that writhe and the average number of writhes per mouse.

Analgesia is measured by inhibition or reduction in writhing, with the degree of analgesic activity being measured by the difference in the average number of writhes between the control animals (animals receiving by gavage an aqueous vehicle with no active medication) and the test animals (animals receiving active agents - either individually or in combination).

EXAMPLES I – II

These Examples illustrate the enhanced analgesic activity which can be obtained with a mixture of d 2-(6-methoxy-2-naphthyl)propionic acid and codeine sulfate. The results of the mouse writhing tests are given in Table I below.

Table I

The Analgesic Activity of Orally Administered Doses of d 2-(6-methoxy-2-naphthyl)propionic acid and Codeine Sulfate Given in Combination

| Ex. | Agent(s) | Dose mg. | No. of Mice | No. of Mice That Writhe | Total Writhes | Mean No. of Writhes | % Change in Writhing |
|---|---|---|---|---|---|---|---|
| — | Control | — | 10 | 9 | 222 | 22.2 | — |
| — | (1) | 0.01 | 10 | 10 | 274 | 27.4 | +23 |
|   |     | 0.02 | 10 | 10 | 207 | 20.7 | −7 |
| — | (2) | 0.05 | 10 | 9 | 205 | 20.5 | −8 |
|   |     | 0.1  | 10 | 9 | 215 | 21.5 | −3 |
| I | (1) | 0.01 | 10 | 7 | 119 | 11.9 | −46 |
|   | (2) | 0.05 |    |   |     |      |     |
| II | (1) | 0.02 | 10 | 10 | 148 | 14.8 | −33 |
|   | (2) | 0.1  |    |   |     |      |     |

(1)= d 2-(6-methoxy-2-naphthyl)propionic acid
(2)= Codeine Sulfate

Thus, it can be seen that when doses of codeine sulfate and d 2-(6-methoxy-2-naphthyl)propionic acid, which by themselves do not inhibit writhing, are combined and given together, the combination is effective in inhibiting writhing. For example, in Table I, it can be seen that 0.01 mg. d 2-(6-methoxy-2-naphthyl)propionic acid in combination with 0.05 mg. codeine sulfate elicited a 46% inhibition of writhing, whereas when given alone these doses are ineffective. In contrast, double the ineffective dose of d 2-(6-methoxy-2-naphthyl)propionic acid or double the ineffective dose of codeine sulfate, each given alone, are still ineffective in inhibiting writhing. This clearly suggests synergism of the combination as opposed to additive effect.

EXAMPLE III

This Example illustrates the enhanced analgesic activity which can be obtained with a mixture of d 2-(6-methoxy-2-naphthyl)propionic acid and the hydrochloride salt of propoxyphene. The results of the mouse writhing tests are given in Table II below.

Table II

The Analgesic Activity of Orally Administered Doses of d 2-(6-methoxy-2-naphthyl)propionic acid and Propoxyphene Hydrochloride Given in Combination

| Ex. | Agent(s) | Dose mg. | No. of Mice | No. of Mice That Writhe | Total Writhes | Mean No. of Writhes | % Change in Writhing |
|---|---|---|---|---|---|---|---|
| — | Control | — | 10 | 10 | 238 | 23.8 | — |
| — | (1) | 0.02 | 10 | 10 | 242 | 24.2 | +2 |
| — | (3) | 0.5 | 10 | 10 | 258 | 25.8 | +8 |
| III | (1) | 0.02 | 10 | 9 | 120 | 12.0 | −50 |
|  | (3) | 0.5 |  |  |  |  |  |

(1) = d 2-(6-methoxy-2-naphthyl)propionic acid
(3) = propoxyphene hydrochloride

Thus, it can be seen that an ineffective amount of d 2-(6-methoxy-2-naphthyl)propionic acid and an ineffective amount of propoxyphene hydrochloride when combined are effective in reducing writhing.

In the following Examples, the analgesic activity of various formulations including d 2-(6-methoxy-2-naphthyl)propionic acid and either α-d-propoxyphene or codeine sulfate is compared with the analgesic activity of the compounds used individually. The test used is a mouse hot plate test, which makes use of a hot plate apparatus consisting of a 9 ½" × 6 ½inch tin can filled with a 50-50 mixture of ethyl formate and acetone. A hot is cut in the upper surface of the can to allow for vaporization of the liquid upon heating. A second hole is made for a thermometer and both holes are sealed with rubber stoppers placed around the condenser and the thermometer. The can is placed on a hot plate and the liquid heated to a constant temperature of 55°C (the boiling point of the mixture of ethyl formate and acetone).

Male Horton ICR mice (18–24 g.) in groups of 10 are used. An open plastic box is placed on the can to contain the mice. Each animal is individually placed on the hot plate and the time from being dropped on the hot plate until it "drums" its hind feet on the can or jumps to the top of the box is recorded. Each animal is tested three times, at one half-hour intervals. Two hours after the start of the experiment the animal is given the test compound or test formulation at the stated dose, i.p. (Example IV) or p.o. (Example V). Each animal is then tested three more times at the half-hour intervals beginning immediately after administration of the active material.

A material is judged to be effective if the time duration before a pain response is evoked in the mouse, at any testing period after an active material is administered, is two or more times longer than the mean of the time duration before the active material is administered.

EXAMPLE IV

This Example illustrates the enhanced analgesic activity, as represented by an increase in the time until "drumming" occurs (i.e., an increase in threshold response), which can be obtained with a mixture of d-(6-methoxy-2-naphthyl)propionic acid and the hydrochloride salt of propoxyphene. The results of the mouse hot plate experiment are given in Table III below.

Table III

| Ex. | Agents | Dose, I.P. mg./kg. | Threshold Increase 2hr. | 2 ½ hr. | 3hr. |
|---|---|---|---|---|---|
| — | (1) | 100 | 0/10 | 0/10 | 0/10 |
| — | (3) | 20 | 0/10 | 1/10 | 1/10 |
| IV | (1) + (3) | 100 + 20 | 7/10 | 6/10 | 2/10 |

(1) = d 2-(6-methoxy-2-naphthyl)propionic acid
(3) = propoxyphene hydrochloride

Thus, it can be seen that an ineffective amount of d 2-(6-methoxy-2-naphthyl)propionic acid and an ineffective amount of propoxyphene hydrochloride when combined show enhanced analgesic activity.

EXAMPLE V

In this Example ED$_{50}$ is the amount of an active material which produces significant analgesia in 50% of the animals tested, in this case, as measured by prolongation of the time until the animal "drums" his hind feet.

This Example illustrates the reduction in the amount of codeine sulfate which has to be administered to attain the ED$_{50}$ obtained with the codeine sulfate alone, such reduction being caused by the enhanced analgesia which can be attained by combining d 2-(6-methoxy-2-naphthyl)propionic acid with codeine sulfate. The results of this mouse hot plate experiment are given in Table IV below.

Table IV

| Ex. | Agents | No. of animals | Codeine Dose levels (mg/kg),P.O. | Codeine ED$_{50}$(mg/kg) |
|---|---|---|---|---|
| — | (1)(100 mg/kg) | 10 | Inactive |  |
| — | (1)(250 mg/kg) | 10 | Inactive |  |
| — | (2) | 40 | 20–80 | 36 |
| — | (2) + (1)(100 mg/kg) | 47 | 5–40 | ≧36 |
| V | (2) + (1)(250 mg/kg) | 47 | 5–40 | 8 |

(1) = d 2-(6-methoxy-2-naphthyl)propionic acid
(2) = codeine sulfate

Thus, it can be seen that an ineffective amount of d 2-(6-methoxy-2-naphthyl)propionic acid when combined with codeine sulfate is effective to reduce the amount (by a factor of about 4.5) of codeine sulfate which has to be administered to attain the $ED_{50}$ obtained with the codeine sulfate alone. The results of this experiment also show that not all dose levels of d 2-(6-methoxy-2-naphthyl)propionic acid give the desired enhanced analgesia with a constant amount of codeine sulfate. The amount of d 2-(6-methoxy-2-naphthyl)-propionic acid which will give the desired result of enhanced analgesia can be determined by routine pharmaceutical or pharmacological experimentation, for example, by use, inter alia, of the tests set forth in the Examples above.

The preceding results, as shown in Tables I-IV, are indicative of the enhanced analgesic activity which can be attained with combinations of d 2-(6-methoxy-2-naphthyl)propionic acid and a central nervous system active analgesic compound such as codeine sulfate and propoxyphene hydrochloride. Since, however, the activities of these compounds vary, it may be necessary to conduct certain routine tests, such as the tests described in the Examples above, in order to accurately define a dose for each component of the mixture which will afford enhanced analgesic activity for the combined formulation. If, for example, the dose for each compound (or both compounds) is (are) selected too low, then enhanced analgesic activity may not be attained; however, by increasing the dosage for each component (or both) to a higher level(s) enhanced analgesic activity for the combined formulation should be attained.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. An analgesic formulation comprising, as a first component, about 50 to about 750 mg. of d 2-(6-methoxy-2-naphthyl)propionic acid, or a pharmaceutically acceptable salt thereof, and, in combination therewith, as a second component, a central nervous system active analgesic compound selected from the group consisting of codeine, propoxyphene, or a pharmaceutically acceptable salt thereof; said components being present in the ratio of about 0.2 parts by weight of said second component, expressed as propoxyphene hydrochloride, or about 0.02 to about 0.16 part by weight of said second component, expressed as codeine sulfate, per part by weight of said first component, expressed as d 2-(6-methoxy-2-naphthyl)propionic acid; said formulation exhibiting enhanced analgesic activity over that which can be obtained utilizing either of said components alone.

2. The formulation of claim 1 wherein said central nervous system active analgesic compound is codeine.

3. The formulation of claim 1 wherein said central nervous system active analgesic compound is codeine sulfate.

4. The formulation of claim 1 wherein said central nervous system active analgesic compound is propoxyphene.

5. The formulation of claim 1 wherein said central nervous system active analgesic compound is propoxyphene hydrochloride.

6. The formulation of claim 1 wherein said first component capsules d 2-(6-methoxy-2-naphthyl)propionic acid.

7. The formulation of claim 1 wherein said formulation contains about 50 to about 750 mg. of the sodium salt of d 2-(6-methoxy-2-naphthyl)propionic acid.

8. The formulation of claim 1 further including a nontoxic pharmaceutically acceptable carrier in combustion therewith.

9. A method of treating a mammal to relieve pain which comprises administering to said mammal a therapeutically effective amount of an analgesic formulation comprising, as a first component, about 50 to about 750 mg. of d 2-(6-methoxy-2-naphthyl)propionic acid, or a pharmaceutically acceptable salt thereof, and, in combination therewith, as a second component, a central nervous system active analgesic compound selected from the group consisting of codeine, propoxyphene, or a pharmaceutically acceptable salt thereof; said components being present in the ratio of about 0.2 part by weight of said second component, expressed as propoxyphene hydrochloride, or about 0.02 to about 0.16 by weight of said second component, expressed as codeine sulfate, per part by weight of said first component, expressed as d 2-(6-methoxy-2-naphthyl)propionic acid; said formulation exhibiting enhanced analgesic activity over that which can be obtained utilizing either of said components alone.

10. The method of claim 9 wherein said central nervous system active analgesic compound is codeine.

11. The method of claim 9 wherein said central nervous system active analgesic compound is codeine sulfate.

12. The method of claim 9 wherein said formulation further includes a non-toxic pharmaceutically acceptable carrier in combination therewith.

13. The method of claim 9 wherein said central nervous system active analgesic compound is propoxyphene.

14. The method of claim 9 wherein said central nervous system active analgesic compound is propoxyphene hydrochloride.

15. The method of claim 9 wherein said first component comprises d 2-(6-methoxy-2-naphthyl)propionic acid.

16. The method of claim 9 wherein said first component comprises the sodium salt of d 2-(6-methoxy-2-naphthyl)propionic acid.

* * * * *

UNITED STATES PATENT OFFICE
CERTIFICATE OF CORRECTION

Patent No. 3,936,528   Dated February 3, 1976

Inventor(s) MARTIN KATZ

It is certified that error appears in the above-identified patent and that said Letters Patent are hereby corrected as shown below:

Column 5, line 29, "hot" should read -- hole --. Claim 6, line 2, "capsules" should read -- comprises --. Claim 7, lines 1-2, "formulation contains about 50 to about 750 mg. of" should read -- first component comprises --. Claim 8, lines 1-2, "combustion" should read -- combination --.

Signed and Sealed this eighteenth Day of May 1976

[SEAL]

Attest:

RUTH C. MASON
Attesting Officer

C. MARSHALL DANN
Commissioner of Patents and Trademarks